(12) United States Patent
Legloahec et al.

(10) Patent No.: US 6,352,966 B1
(45) Date of Patent: Mar. 5, 2002

(54) CLEANSING BARS

(75) Inventors: Valerie N. Legloahec; Patrick C. Hu, both of Baton Rouge; Deborah A. Quebedeaux, Thibodaux; Conrad J. Langlois, Jr., New Roads, all of LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/574,280

(22) Filed: May 19, 2000

(51) Int. Cl.$^7$ ................................................. A61K 7/50
(52) U.S. Cl. .................. 510/156; 510/152; 510/155; 510/447; 510/492
(58) Field of Search ................................ 510/151, 152, 510/153, 155, 156, 447, 492

(56) References Cited

U.S. PATENT DOCUMENTS

| | | | |
|---|---|---|---|
| 3,178,370 A | 4/1965 | Okenfuss | 252/137 |
| 4,277,378 A | 7/1981 | Tsujii et al. | 252/546 |
| 4,493,786 A | 1/1985 | Joshi | 252/368 |
| 4,574,053 A | 3/1986 | Kinsman et al. | 252/134 |
| 4,959,171 A | 9/1990 | Pantini et al. | 252/174 |
| 4,963,284 A | 10/1990 | Novakovic et al. | 252/108 |
| 5,229,028 A | 7/1993 | Boutique et al. | 252/142 |
| 5,294,363 A | 3/1994 | Schwartz et al. | 252/108 |
| 5,300,249 A | 4/1994 | Schwartz et al. | 252/108 |
| 5,310,508 A | 5/1994 | Subramanyam et al. | 252/549 |
| 5,543,072 A | 8/1996 | Fost et al. | 510/151 |
| 5,719,116 A | 2/1998 | Vanweissenaiers et al. | 510/434 |
| 5,981,452 A | 11/1999 | Schrader et al. | 510/155 |

FOREIGN PATENT DOCUMENTS

| | | |
|---|---|---|
| EP | 0028850 | 5/1981 |
| EP | 0212723 | 3/1987 |
| GB | 2049723 | 12/1980 |
| GB | 2188645 | 10/1987 |
| WO | 9853040 | 11/1998 |
| WO | 9855584 | 12/1998 |

OTHER PUBLICATIONS

Berna et al., "Laundry Products in Bar Form", Journal of Surfactants and Detergents, 1998, vol. 1, No. 2, pp. 263–271, *NMA.
WPIDS Abstract of JP 10324899, 1998, *NMA.
CAPLUS Abstract of JP 10324899 A2, 1998, *NMA.
CAPLUS Abstract of JP 60054337, issued 1985, *NMA.

*Primary Examiner*—Necholus Ogden
(74) *Attorney, Agent, or Firm*—Philip M. Pippenger

(57) ABSTRACT

The cleansing bar is comprised of at least one fully neutralized alkali metal salt of an alkyl or alkenyl succinic acid in which the alkyl or alkenyl group is a straight chain alkyl or alkenyl group containing about 8–14 carbon atoms.

12 Claims, No Drawings

CLEANSING BARS

TECHNICAL FIELD

This invention relates to novel shaped cleansing compositions such as bars or cakes of enhanced performance qualities in which at least a portion of the composition is comprised of a synthetic surface active ingredient.

BACKGROUND

Although widely used for over a century, fatty acid soaps are known to possess certain shortcomings. For one thing, fatty acid soaps are inefficient cleaning agents, in that, in aqueous systems the surface tension of the soaps is higher than desired, and the grease-cutting efficiency of the soaps is inadequate. Moreover, fatty acid soaps have very poor tolerance to hard water, and thus produce little if any suds and form soap scums when used with hard water.

Over the years, numerous attempts have been made to circumvent the foregoing deficiencies of the fatty acid soaps by utilization of synthetic surface active ingredients in the manufacture of so-called "syndet" bars composed entirely of synthetic surface active ingredients, and "combo" bars composed in part of synthetic surface active ingredients and in part of the fatty acid soap. Although these approaches have overcome many of the shortcomings of fatty acid soaps, the use of syndet and combo bars has given rise to new shortcomings. Among such shortcomings are unacceptable slough rates, harshness to skin, and loss of structural integrity during use. Also, in many cases the costs associated with production of syndet bars or combo bars are higher than desirable. Consequently, there remains a need for soaps comprised of one or more synthetic surface active ingredients with superior performance qualities which can be achieved at relatively modest costs.

This invention is deemed to fulfill the foregoing need in a highly efficient manner.

U.S. Pat. No. 4,277,378 describes an alkaline builder-free detergent composition containing a partially neutralized succinic acid derivative in which the succinic acid moiety is substituted by a saturated or unsaturated hydrocarbon group having 8–18 carbon atoms, such as an alkenyl group that can be branched or straight chain. In Examples 7 and 8 syndet bars were made from formulations containing partially neutralized di- or triethanolamine salts of tetradecenyl succinic acid. These bars are reported to have excellent foaming properties and to be comfortable when used.

Test work performed in our laboratories, indicates that fully neutralized triethanolamine salts of straight chain alkyl or alkenyl succinic acids are tacky substances.

THE INVENTION

Pursuant to this invention, it has been found possible to provide cleansing bars comprised of one or more particular surface active ingredients, which bars have a number of superior performance qualities. Moreover, these advantages can be achieved with materials that can be readily produced from readily-available raw materials at relatively modest costs.

This invention provides in one of its embodiments a cleansing bar comprised of at least one fully neutralized alkali metal salt of an alkyl or alkenyl succinic acid in which the alkyl or alkenyl group is a straight chain alkyl or alkenyl group containing in the range of about 8 to about 14 carbon atoms. The sodium and potassium salts are preferred, with the sodium salt being most preferred. Unlike the fully neutralized triethanolamine salts, the fully neutralized alkali metal succinate salts, especially the fully neutralized sodium salts, are completely free of tackiness.

The cleansing bars of this invention on an anhydrous basis will typically comprise in the range of about 5 to 100 wt %, and preferably in the range of about 10 to 100 wt % of one or more of the alkyl and/or alkenyl succinic acid salts (often referred to hereinafter collectively as "alk(en)yl succinic acid salts"). Typically, the cleansing bars of this invention will contain up to about 15 wt % of water, either as free water or as water of hydration, or both.

The alk(en)yl succinic acid salts used pursuant to this invention are white, high-melting solids which at room temperature are highly-crystalline whereas at mildly elevated temperatures often used in preparation of commercial cleansing bars (e.g., 50–80° C.) can be easily compounded with other ingredients (if desired) and shaped into the desired form. Moreover, when in the form of bars or cakes, such alk(en)yl succinic acid salts have considerable structural integrity at room temperature. In addition, such bars or cakes exhibit excellent lathering in all types of water, low wear rates, good tactile properties, minimal slushing and curd-forming properties in all types of water, and mildness to the user's skin. Further, such bars are resistant to becoming mushy and susceptible to excessive sloughing upon standing in a soap dish in contact with water.

Other ingredients can be included in the cleansing bars and cakes of this invention. By way of example, depending upon the intended use of the bar or cake, there may be combined therewith one or more other types of surfactants, including known anionic, nonionic, zwitterionic, or amphoteric surfactants, as well as one or more conventional fatty acid soaps. In this connection, the most important fatty acid based compositions that may be used as the soap base in the bars or cakes of this invention are stearic acid, coco fatty acids, and tallow fatty acids, as well as mixtures of these fatty acids. Such fatty acids can be fully or partially hydrogenated. The more common of these mixtures are those containing tallow:coco fatty acid ratios of 80:20, 85:15, 70:30 and 50:50, with tallow:coco fatty acid ratios of 80:20 and 85:15 being the most common.

The soap bars of this invention may also contain about 3 to about 15 wt %, and more preferably about 4 to about 6 wt %, glycerine. Superfatting agents may also be used in the soap bars of this invention. These superfatting agents include unneutralized fatty acids, fats, and oils and mineral oils. The fatty acids are the more preferred of such agents. The superfatting agents are preferably used in amounts of about 3 to about 6 wt %, but amounts of up to about 10 to about 15 wt % may also be used.

Other additives commonly employed in the soap bar-making arts may also be used in the soap bars of this invention, for example, colorants, such as $TiO_2$, perfumes, stabilizers, bacteriostats (e.g., as deodorants or germicides), and processing aids such as common salts. All of these other additive materials are used at levels of up to about 1 wt %, except for perfumes which may be used at levels of up to about 2 to about 3 wt %.

If it is desired to include other surfactants in the cleansing bars of this invention, preferred surfactants for this purpose include alkali metal salts of acyl isethionates, fatty alcohol sulfates and alkane sulfonates, alone, or in the various admixtures thereof. Other surfactants that may be used include, for example, sodium lauryl sulfoacetate, fatty acid sarcosinates, sodium lauryl glyceryl sulfonate and sodium dodecyl benzene sulfonate. The surfactants are used in the cleansing bars of this invention at a level of about 15 to about 70 wt %, and preferably in the range of about 15 to about 20 wt %, based on a solids content basis.

Fillers that may be used in the syndet or combo bars of this invention are water-insoluble inorganic materials having an average particle size of about 0.05 to about 20 microns, and preferably of about 0.5 to about 5.0 microns. The fillers are preferably pretreated by being ground to achieve the desired particle size, if necessary, and/or they may be chemically-precipitated to provide a desired particle size.

Another advantageous feature of this invention is that the above-described cleansing bars and cakes can be produced using any one of the conventional soap-making techniques. Such techniques are well known to those skilled in the art and are reported in the literature. See for example U.S. Pat. No. 3,178,370 to Okenfuss, et al., and Berna et al., *Journal of Surfactants and Detergents,* Vol. 1, No. 2, pages 263–271 (April 1998).

The following examples are presented for illustrative purposes and are not to be construed as limiting the scope of this invention to only that which is described therein.

EXAMPLE 1

Preparation of n-Tetradecenyl Succinic Anhydride

A nitrogen-dried 1-Liter Büchi stainless steel reactor, equipped with a mechanical stirrer, a thermocouple well and a nitrogen inlet tube, is charged with maleic anhydride (99 g; 1 eq.) and $C_{14}$ α-olefin (304 g; 1.55 eq.). The vessel is then bolted to the reactor frame and the reaction mixture is purged with nitrogen for 15 minutes. The mixture is stirred with a double helical impeller at 900 rpm and heated with an oil bath on the reactor jacket. The mixture reaches 225° C. at a pressure of 60 psi in about 40 minutes. After 2.5 hours at 230° C., the hot amber liquid is quickly discharged through the bottom valve of the reactor into a 2-L Erlenmeyer flask under a nitrogen atmosphere. Volatiles (excess olefin and unreacted maleic anhydride) are stripped from the reaction mixture using a 4-L Kügelrohr apparatus up to a final pot temperature of 110° C. at 0.5 mm Hg or 0.5 Torr. The resulting material is then distilled under reduced pressure (bp ca. 200–220° C. at ca. 1 mm Hg) to yield after cooling to room temperature a white pasty solid melting in the range of 42–45° C.

Preparation of a Bar of the Disodium Salt of n-Tetradecenyl Succinic Acid n-Tetradecenyl Succinic Anhydride (1 mole) is melted with an external heating source and poured into a high shear mixer, together with a concentrated aqueous solution of sodium hydroxide (2 moles) to achieve complete mixing. The reaction is exothermic, reaching approximately 150° C. with formation of steam. The resultant hot mixture has the consistency of a soft paste or dough. Upon molding and cooling, a hard cleansing bar of fully neutralized sodium n-tetradecenyl succinate is formed.

EXAMPLE 2

Preparation of n-Octenyl Succinic Anhydride and a Bar of the Disodium Salt of n-Octenyl Succinic Acid Using the general procedure described in Example 1, an alkenyl succinic anhydride is formed from 1-octene. A portion of this product (1 mole), a liquid at room temperature, is poured into a high shear mixer together with 2 moles of concentrated aqueous sodium hydroxide solution to achieve complete mixing. The resultant hot soft pasty product is molded and cooled to form a hard cleansing bar of fully neutralized sodium n-octenyl succinate.

EXAMPLE 3

Preparation of-Octyl Succinic Anhydride and a Bar of the Disodium Salt of n-Octyl Succinic Acid Using the general procedure described in Example 1, an alkenyl succinic anhydride is formed from 1-octene. This product, a liquid at room temperature, is converted to octyl succinic anhydride using the following procedure. A nitrogen-dried 500-mL Parr hydrogenation bottle is charged with 10 g of the octenyl succinic anhydride, 20 g of ethyl acetate and 0.26 g of 10% by weight of palladium on activated carbon. The vessel is then bolted to the reactor frame and the reactor is pressured to 20 psi with hydrogen. The reaction mixture is shaken for 30 seconds and then the pressure is released. This hydrogen charging, shaking, and discharging procedure is repeated several times. The reactor is then again charged with 20 psi of hydrogen and the mixture is shaken and heated at ca. 50° C. with an electrical mantle on the reactor jacket. At the end of the reaction (when no further uptake of hydrogen occurs) the reactor is discharged. The reaction mixture is filtered through a short pad of Celite® filtering aid to remove the catalyst. Then the reaction mixture is concentrated under reduced pressure with the formation of an essentially quantitative yield of a white solid melting in the range of 59–61° C. A one mole portion of this product is poured into a high shear mixer together with 2 moles of concentrated aqueous sodium hydroxide solution to achieve complete mixing. The resultant hot soft pasty product is molded and cooled to form a hard cleansing bar of fully neutralized sodium n-octyl succinate.

EXAMPLE 4

The efficacy of the fully neutralized sodium salts of various n-alk(en)yl succinates is demonstrated by determining the surface tension of four different disodium alk(en)yl succinates as measured in an ionic buffer solution composed of 0.02 normal aqueous potassium nitrate solution at 25° C. The fully neutralized succinates tested and the surface tensions in millinewtons per meter are summarized in Table 1. Also shown in Table 1 are the corresponding values for the partially neutralized monosodium salts of the corresponding alk(en)yl succinic acids.

TABLE 1

| | |
|---|---|
| Disodium n-octylsuccinate | 26 |
| Disodium n-decylsuccinate | 26 |
| Disodium n-dodecenylsuccinate | 25.8 |
| Disodium n-tetradecenylsuccinate | 26 |
| Monosodium n-octylsuccinate | 26.64 |
| Monosodium n-decylsuccinate | 26.32 |
| Monosodium n-dodecenylsuccinate | 26.32 |
| Monosodium n-tetradecenylsuccinate | 26 |

The data in Table 1 indicate that all such succinates are effective surfactants.

EXAMPLE 5

The desirable properties of cleansing bars formed from fully neutralized sodium salts of various alkenyl succinic acids of this invention were determined in a further series of comparative tests. In these tests both the reflectance and the bar hardness were determined. In addition to testing bars of five different fully neutralized succinate salts of this invention, the same properties were measured on four fully compounded commercial soap bars from different well-known soap manufacturers. As can be appreciated, the higher the reflectance the whiter the bar, and the higher the hardness, the more desirable is the bar. Table 2 summarizes the results of these tests. In Table 2, the five fully neutralized alkenyl succinic acids are identified in terms of the number of carbon atoms in the alkenyl group. Thus, for example, C6 SAS represents the fully neutralized disodium salt of n-hexenyl succinic acid. As regards reflectance, Commercial Bar B is pink in color, and Commercial Bar C is a coral-orange in color. The other two commercial bars are white.

TABLE 2

| Bar Tested | Reflectance | Bar Hardness |
| --- | --- | --- |
| C6 SAS | 92 | 88 |
| C8 SAS | 92 | 104 |
| C10 SAS | 88 | 115 |
| C12 SAS | 87 | 132 |
| C14 SAS | 74 | 144 |
| Commercial A | 96 | 165 |
| Commercial B | 71 | 130 |
| Commercial C | 74 | 120 |
| Commercial D | 90 | 139 |

The blocks of this invention can be of any geometric shape or configuration, such as, for example, cubes, slabs, pyramids, spheres, dumbbells, doughnuts, cones, cylinders, toroids, strands, hemispheres, and teardrops. The volume of the individual bars and blocks of this invention is typically at least about 20 cubic centimeters and preferably is at least about 50 cubic centimeters. There is no hard and fast upper limit to their volume as this depends on the use to which the bars or blocks are to be put. Often the bars will have a volume comparable to the volume of the conventional soap bars, but this invention includes huge molded or casted slabs or blocks, or extrudates, which are to be cut into smaller shapes, such as hand cleansing bars or the like.

Compounds referred to by chemical name or formula anywhere in this document, whether referred to in the singular or plural, are identified as they exist prior to coming into contact with another substance referred to by chemical name or chemical type (e.g., another component, a solvent, or etc.). It matters not what preliminary chemical changes, if any, take place in the resulting mixture or solution, as such changes are the natural result of bringing the specified substances together under the conditions called for pursuant to this disclosure. Also, even though the claims may refer to substances in the present tense (e.g. "comprises", "is", etc.), the reference is to the substance as it exists at the time just before it is first contacted, blended or mixed with one or more other substances in accordance with the present disclosure.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A cleansing bar or cake comprised of at least one compound selected from the group consisting of (i) one or more fully neutralized alkyl succinic acid alkali metal salts in which the alkyl group is a straight chain alkyl group containing in the range of about 8 to about 14 carbon atoms, and (ii) one or more fully neutralized alkenyl succinic acid alkali metal salts in which the alkenyl group is a straight chain alkenyl group containing in the range of about 8 to about 14 carbon atoms.

2. A cleansing bar or cake of claim 1 wherein the alkali metal of said at least one compound is sodium or potassium.

3. A cleansing bar or cake of claim 1 wherein said at least one compound is the disodium salt of n-octenyl succinic acid, the disodium salt of n-decenyl succinic acid, the disodium salt of n-dodecenyl succinic acid, the disodium salt of n-tetradecenyl succinic acid, or a mixture of any two or more of these.

4. A cleansing bar or cake of any of claims 1, 2, or 3 wherein said bar or cake is comprised on an anhydrous basis of about 10 to 100 wt % of said at least one compound.

5. A cleansing bar or cake of any of claims 1, 2, or 3 wherein said bar or cake is comprised on an anhydrous basis of about 100 wt % of said at least one compound.

6. A cleansing bar or cake of any of claims 1, 2, or 3 wherein said bar or cake contains up to about 15 wt % of water, either as free water or as water of hydration, or both.

7. A cleansing bar or cake of any of claims 1, 2, or 3 wherein said bar or cake consists of said at least one compound and up to about 15 wt % of water, either as free water or as water of hydration, or both.

8. A cleansing bar or cake of claim 1 wherein the alkali metal of said at least one compound is sodium.

9. A cleansing bar or cake of claim 8 wherein said bar or cake is comprised on an anhydrous basis of about 10 to 100 wt % of said at least one compound.

10. A cleansing bar or cake of claim 8 wherein said bar or cake is comprised on an anhydrous basis of about 100 wt % of said at least one compound.

11. A cleansing bar or cake of claim 8 wherein said bar or cake contains up to about 15 wt % of water, either as free water or as water of hydration, or both.

12. A cleansing bar or cake of claim 8 wherein said bar or cake consists essentially of said at least one compound and up to about 15 wt % of water, either as free water or as water of hydration, or both.

* * * * *